United States Patent
Bawa et al.

(10) Patent No.: US 6,174,524 B1
(45) Date of Patent: Jan. 16, 2001

(54) GELLING OPHTHALMIC COMPOSITIONS CONTAINING XANTHAN GUM

(75) Inventors: Rajan Bawa, Fort Collins, CO (US); Rex E. Hall, Fort Worth, TX (US); Bhagwati P. Kabra; James E. Teague, both of Arlington, TX (US)

(73) Assignee: Alcon Laboratories, Inc., Fort Worth, TX (US)

( * ) Notice: Under 35 U.S.C. 154(b), the term of this patent shall be extended for 0 days.

(21) Appl. No.: 09/277,102

(22) Filed: Mar. 26, 1999

Related U.S. Application Data

(60) Provisional application No. 60/081,004, filed on Apr. 7, 1998.

(51) Int. Cl.[7] .................................................... A61K 31/74
(52) U.S. Cl. ........................................ 424/78.04; 514/912
(58) Field of Search ........................ 424/78.04; 514/912

(56) References Cited

U.S. PATENT DOCUMENTS

| | | | |
|---|---|---|---|
| 3,700,451 | 10/1972 | Sullivan, Jr. | 96/66 |
| 3,784,712 | 1/1974 | Glicksman et al. | 426/167 |
| 3,944,427 | 3/1976 | Sullivan, Jr. | 106/208 |
| 4,135,979 | 1/1979 | Corley et al. | 195/31 |
| 4,136,173 | 1/1979 | Pramoda et al. | 424/177 |
| 4,136,177 | 1/1979 | Lin et al. | 424/211 |
| 4,136,178 | 1/1979 | Lin et al. | 424/211 |
| 4,638,059 | 1/1987 | Sutherland | 536/121 |
| 4,647,470 | 3/1987 | Sanderson et al. | 426/573 |
| 4,661,475 | 4/1987 | Bayerlein et al. | 514/54 |
| 4,708,861 | 11/1987 | Popescu et al. | 424/1.1 |
| 4,717,713 | 1/1988 | Zatz et al. | 514/2 |
| 4,775,632 | 10/1988 | Gozard et al. | 435/104 |
| 4,861,760 | 8/1989 | Mazuel et al. | 514/54 |
| 4,996,197 | 2/1991 | Mazuel | 514/54 |
| 5,212,162 | 5/1993 | Missel et al. | 514/54 |
| 5,234,957 | 8/1993 | Mantelle | 514/772.6 |
| 5,318,780 | 6/1994 | Viegas et al. | 424/427 |
| 5,403,841 | 4/1995 | Lang et al. | 514/226.8 |
| 5,422,116 | 6/1995 | Yen et al. | 424/427 |
| 5,446,070 | 8/1995 | Mantelle | 514/772.6 |
| 5,461,081 | 10/1995 | Ali et al. | 514/772.3 |
| 5,462,749 | 10/1995 | Rencher | 424/484 |
| 5,473,062 | 12/1995 | Haze et al. | 536/114 |
| 5,493,015 | 2/1996 | Murofushi et al. | 536/127 |
| 5,587,175 | 12/1996 | Viegas et al. | 424/427 |
| 5,618,800 | 4/1997 | Kabra et al. | 514/57 |
| 5,759,563 | 6/1998 | Yewey et al. | 424/426 |

FOREIGN PATENT DOCUMENTS

| | | |
|---|---|---|
| 1070629 | 1/1980 | (CA) . |
| 0 331 617 A1 | 6/1989 | (EP) . |
| 0 374 658 A2 | 12/1989 | (EP) . |
| 0 410 326 A2 | 7/1990 | (EP) . |
| 0 424 043 A1 | 10/1990 | (EP) . |
| 0 424 043 B1 | 5/1993 | (EP) . |
| 0 780 121 A1 | 12/1996 | (EP) . |
| 96/03990 | 2/1996 | (WO) . |
| 98/11874 | 3/1998 | (WO) . |
| 98/17249 | 4/1998 | (WO) . |
| WO 98/53809 | 12/1998 | (WO) . |
| WO 99/00133 | 1/1999 | (WO) . |

OTHER PUBLICATIONS

Selby et al., *Industrial Gums*, 3rd Edition, R. L. Whistler and J.N. BeMiller, eds., Academic press, San Diego (1993), Chapter 5 "Agar", pp. 87–103.

Smith et al., "Influence of the Pyruvate Content of Xanthan on Macromolecular Association in Solution," *Int. J. Biol. Macromol.*, vol. 3, pp. 129–134 (Apr. 1981).

(List continued on next page.)

*Primary Examiner*—Carlos A Azpuru
(74) *Attorney, Agent, or Firm*—Patrick M. Ryan

(57) ABSTRACT

Ophthalmic drug delivery vehicles which are administrable as a liquid and which gel upon contact with the eyes are disclosed. The vehicles contain xanthan gum.

13 Claims, 4 Drawing Sheets

OTHER PUBLICATIONS

Callet et al., "Influence of Acetyl and Pyruvate Contents on Rheological Properties of Xanthan in Dilute Solution," *Int. J. Biol. Macromol.*, vol. 9, pp. 291–293 (Mar. 1987).

Cheetham et al., "An HPLC Method for the Determination of Acetyl and Pyruvyl Groups in Polysaccharides," *Carbohydrate Polymers*, vol. 5, pp. 399–406 (Apr. 1985).

Gamini et al., "Physico–chemical properties of aqueous solutions of xanthan: An n.m.r. study," *Carbohydrate Research*, vol. 220, pp. 33–47 (Mar. 1991).

Smith et al., "Influence of the Pyruvate Content of Xanthan on Macromolecular Association in Solution," *Int. J. Biol. Macromol.*, vol. 3, pp. 129–134 (1981).

Tait et al., "Acid Hydrolysis and High–Performance Liquid Chromatography of Xanthan," *Carbohydrate Polymers*, vol. 13, pp. 133–148 (1990).

Milas et al., "The Effect of Thermal Aging on Xanthan Solutions," *J. of Applied Polymer Science*, vol. 35, pp. 1115–1122 (1988).

Oviatt et al., "Thermal Treatment of Semi–dilute Aqueous Xanthan Solutions Yields Weak Gels with Properties Resembling Hyaluronic Acid," *Int. J. Biol. Macromol.*, vol. 15(3), pp. 3–10.

Sanford et al., "Microbial Polysaccharides: New Products and Their Commercial Applications," *Pure & Appl. Chem.*, vol. 56(7), pp. 879–892 (1984).

McNeely et al., *Industrial Gums*, Academic Press, Inc., San Diego, CA, (1973), Chapter VII. "Xanthan Gum," pp. 486–497.

Meseguer et al., "Gamma Scintigraphic Comparison of Eyedrops Containing Pilocarpine in Healthy Volunteers," *J. of Ocular Pharmacology and Therapeutics*, vol. 12(4), pp. 481–488 (1996).

Meseguer et al., "Gamma Scintigraphic Study of Precorneal Drainage and Assessment of Miotic Response in Rabbits of Various Ophthalmic Formulations Containing Pilocarpine," *International J. of Pharmaceutics*, vol. 95, pp. 229–234 (1993).

Kierulf et al., "Thermal Stability of Xanthan Preparations," *Carbohydrate Polymers*, vol. 9, pp. 185–194 (1988).

Lambert et al., "On the Thermal Stability of Xanthan Gum," *Polymer*, vol. 26, pp. 1549–1553 (1985).

Lund et al., Properties of Xanthan Solutions after Long–Term Heat Treatment at 90° C., *Polymer Degradation and Stability*, vol. 27, pp. 211–225 (1990).

Foss et al., "Thermal Stability and Chain Conformational Studies of Xanthan at Different Ionic Strengths," *Carbohydrate Polymers*, vol. 7, pp. 421–433 (1987).

Gamini et al., "Physico–chemical Properties of Aqueous Solutions of Xanthan: An n.m.r. Study," *Carbohydrate Research*, vol. 220, pp. 33–47 (1991).

Kelco Product Brochure, "Xanthan Gum—Natural Biogum for Scientific Water Control," Fifth Edition (1994).

Carrington et al., "Polyelectrolyte Behaviour of Dilute Xanthan Solutions: Salt Effects on Extensional Rheology," *Polymer*, vol. 37 (13); pp. 2871–2875 (1996).

Nolte et al., "Gelation of Xanthan With Trivalent Metal Ions," *Carbohydrate Polymers*, vol. 18(4), pp. 243–251 (1992).

Shatwell et al., "The Influence of Acetyl and Pyruvate Substitutents on the Helix—Coil Transition Behaviour or Xanthan," *Carbohydrate Research*, vol. 206 (1), pp. 87–103 (1990).

US 6,174,524 B1

GELLING OPHTHALMIC COMPOSITIONS CONTAINING XANTHAN GUM

This application claims priority to co-pending U.S. Provisional Application, U.S. Ser. No. 60/081,004, filed Apr. 7, 1998.

BACKGROUND OF THE INVENTION

1. Field of the Invention

The present invention relates to pharmaceutical compositions. In particular, this invention relates to ophthalmic compositions and drug delivery vehicles which are administrable as liquids and which gel upon contact with the eye.

2. Description of Related Art

Although gels are desirable because they prolong the contact or residence time of drugs in the eye, they are not as easy to administer topically as liquid drops. A variety of gelling drug delivery systems have been developed in an effort to allow an ophthalmic pharmaceutical composition to be topically administered as a liquid drop and then gel upon contact with the eye. Drug delivery vehicles containing polysaccharide polymers which gel in response to a pH change have been proposed, such as those described in U.S. Pat. Nos. 4,136,173, 4,136,177, and 4,136,178, for example.

Drug delivery systems which gel in response to temperature changes have also been proposed. For example, drug delivery systems utilizing Tetronic®, Pluronic®, or other polyols have been disclosed in U.S. Pat. Nos. 4,474,751; 4,474,752; and 4,188,373. U.S. Pat. Nos. 5,124,151; 5,306,501 and 5,618,800 also disclose thermally gelling systems.

Alternatively, ion-sensitive gelling polymers have been identified. European Patent No. 0 227 494 B1 discloses ophthalmic compositions containing polysaccharides of the type that undergo liquid-gel phase transition under the effect of an increase in ionic strength. The only representative polysaccharide specifically disclosed by this European patent, however, is gellan gum. U.S. Pat. No. 5,403,841 discloses gelling ophthalmic compositions that contain carrageenans, such as *Eucheuma Carrageenani*. The carrageenan-containing compositions are characterized as capable of gelling in about 0.5 to 1% aqueous NaCl.

International Publication No. WO 92/09307 discloses gelable carrier compositions containing a water-soluble, nonionic cellulose ether polysaccharide, such as ethylhydroxyethylcellulose, and a charged surfactant. The reference compositions gel due to strong hydrophobic interactions between the polymer and the charged surfactant.

Various drug delivery systems employing combinations of two types of gelling polymers have also been disclosed. U.S. Pat. No. 5,077,033 discloses a thermally irreversible gel system comprising a combination of polyoxyalkylene and ionic polysaccharides. U.S. Pat. No. 5,296,228 discloses aqueous reversibly gelling polymeric solutions containing ion exchange resin particles. The polymeric component of the solution may be a pH sensitive polymer, a temperature sensitive polymer, or combinations of both pH-sensitive polymers and temperature sensitive polymers. U.S. Pat. No. 5,252,318 also discloses reversibly gelling aqueous compositions containing combinations of polymers, in this case at least one pH-sensitive reversibly gelling polymer and at least one temperature sensitive reversibly gelling polymer.

U.S. Pat. No. 5,212,162 discloses ophthalmic compositions containing gelling polysaccharides and drug carrier substrates. As used in the '162 patent, gelling polysaccharide means a polysaccharide capable of reversible liquid-to-gel transition based on a change in ionic strength or pH. According to the '162 patent, suitable gelling polysaccharides include xanthan gum, locust bean gum, gellan gum, carrageenans and combinations thereof. The '162 patent references U.S. Pat. Nos. 4,136,173, 4,136,177, and 4,136,178 in connection with xanthan gum and locust bean gum.

EP 0 424 043 A1 discloses liquid ophthalmic compositions that undergo liquid-gel phase transition upon administration to the eye. The compositions comprise an aqueous solution of at least one active agent and are characterized in that they contain 0.1 to 5% by weight of a sulfated polysaccharide derivative, preferably selected from kappa-carrageenan, iota-carrageenan and mixtures thereof, whereby the liquid-gel phase transition is mediated by interaction of the sulfated polysaccharide derivative with the proteins of the lachrymal fluid.

Xanthan gum is a polysaccharide known to be useful in ophthalmic compositions as a viscosity enhancing agent. U.S. Pat. No. 4,136,177 discloses ophthalmic compositions containing an ophthalmic drug and from about 0.01 to 2.5% (w/v) of xanthan gum. The '177 patent teaches that if the concentration of xanthan gum is from about 0.02 to about 1.0% (w/v), the composition is suitable for "dropwise" ophthalmic applications. In contrast, at concentrations of xanthan gum above about 1.0% and up to about 2.5% (w/v), "a gel-like consistency is attained." Thus, the '177 patent discloses compositions that are formulated to be either non-gelled liquids or gels before instillation in the eye. The '177 patent does not describe any xanthan gum-containing compositions as capable of being administered as a liquid and gelling upon contact with the eye.

U.S. Pat. No. 4,136,173 discloses ophthalmic compositions containing a combination of xanthan gum and locust bean gum. These compositions gel due to a change in pH. The '173 patent discloses that, in solutions containing either of these two gums alone, "sufficient gelling did not occur, nor, at the same time, did these solutions demonstrate pH sensitive liquid-gel reversibility." ('173 patent, Col. 4, lines 1–4).

It has been accepted in the art that xanthan gum is not a polymer of the type which is capable of undergoing a liquid-gel phase transition upon contact with the eye. See, for example, Meseguer, et al., Journal of Ocular Pharmacology and Therapeutics, 12(4):481–487 (1996), describing gellan gum as a "phase-transition system" but xanthan gum as a "viscosity enhancer."

SUMMARY OF THE INVENTION

The present invention is directed toward ophthalmic compositions which are administrable as a liquid and which gel upon contact with the eye. The compositions of the present invention contain xanthan gum, but do not contain locust bean gum.

Among other factors, the present invention is based upon the finding that compositions containing xanthan gum as the sole gelling polymer are capable of gelling upon contact with the eye.

Among other factors, the present invention is based upon the finding that xanthan gum gels upon contact with the eye due, at least in part, to an interaction with the lysozyme component of tear fluid.

Among other factors, the present invention is also based upon the finding that the strength of the gel formed by xanthan gum upon contact with lysozyme is dependent upon both the acetate and pyruvate content of xanthan gum.

DETAILED DESCRIPTION OF THE INVENTION

Figure 1:
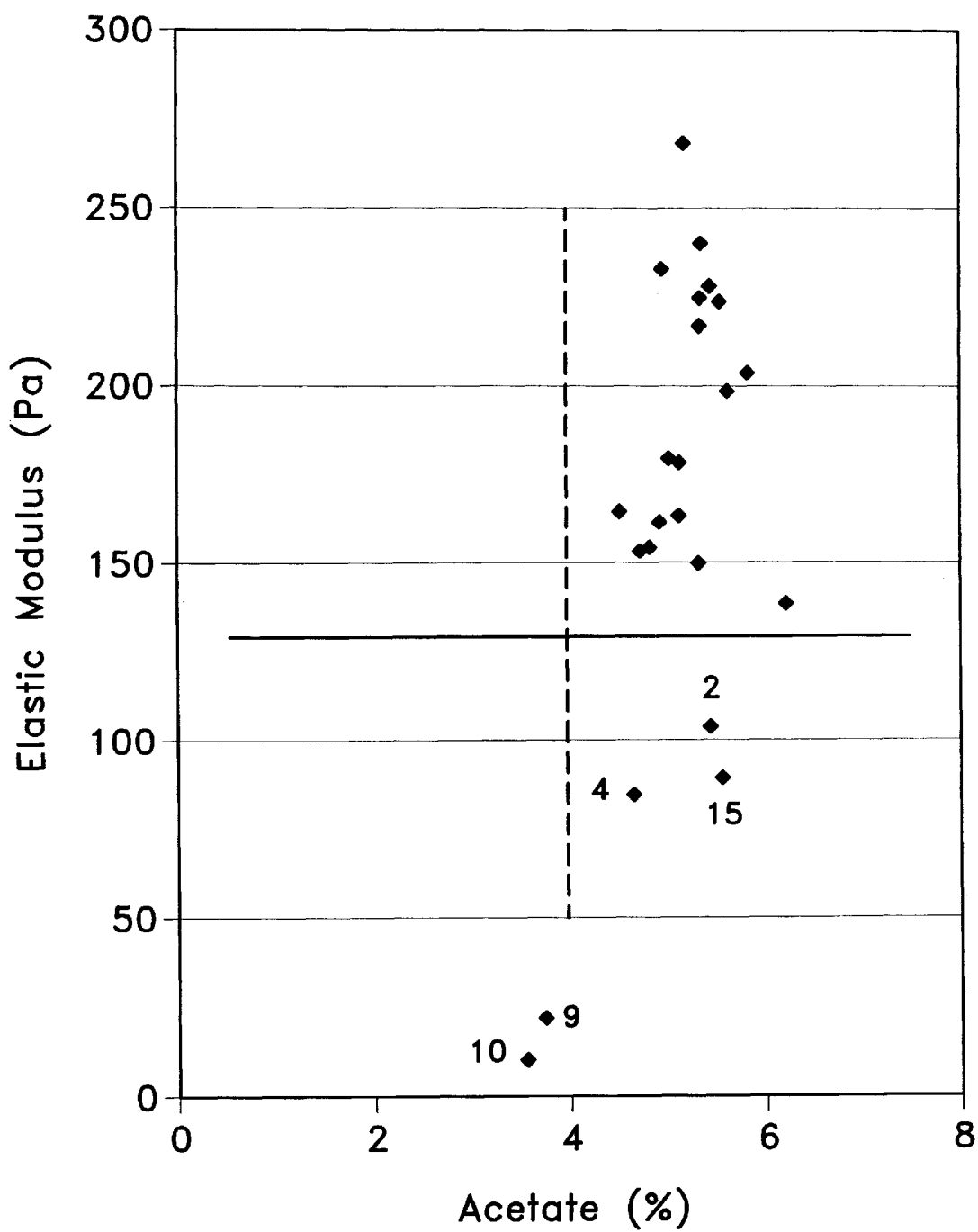
FIG. 1 shows the relationship between elastic modulus (G', Pa) and acetate content for xanthan gum.

The ophthalmic compositions of the present invention are formulated as non-gelled liquids which gel upon instillation in the eye. The compositions contain xanthan gum as a gelling agent, and do not contain locust bean gum. Xanthan gum is a well-known polysaccharide that is commercially available from a variety of sources. The amount of xanthan gum contained in the compositions of the present invention will depend upon the identity and concentration of other ingredients in the composition, but will generally range from about 0.1 to about 1% (w/w).

It is important that the xanthan gum contained in the compositions of the present invention have an initial bound acetate content of at least about 4%. Bound acetate content means the amount of acetate esterified to the xanthan gum molecule (w/w). Bound acetate content can be measured by HPLC methods and may be available from the commercial suppliers of xanthan gum.

It is also important that the xanthan gum have an initial bound pyruvate concentration of at least about 2.5%. The bound pyruvate content means the amount of pyruvate which is bound to the xanthan gum molecule in a ketal form (w/w). The bound pyruvate content can be measured by calorimetric or HPLC methods and is commonly available from the commercial suppliers of xanthan gum.

As used herein, "initial" bound acetate or pyruvate content of xanthan gum means that content present in the raw material as received from the supplier, measured before the expiration date assigned to the raw material by the supplier and prior to any processing or formulating.

The ability of xanthan to form a gel upon contact with the eye can be affected both by the identity and amount of other ingredients in the compositions of the present invention and by subsequent processing steps, such as a steam sterilization step. Once formulated and processed to finished form, the ability of the xanthan gum-containing compositions of the present invention to gel upon contact with the eye may change over time as well, due in part to changes in the bound acetate content over time. By restricting the initial bound acetate and pyruvate content as described above, the xanthan gum raw material to be included in the compositions of the present invention is selected based on its ability to form relatively strong gels—on the order of approximately 130 Pa (elastic modulus, G')-5 when measured using the Lysozyme Gel Strength Test described in Example 1 below.

Ophthalmic drugs suitable for use in the compositions of the present invention include, but are not limited to: anti-glaucoma agents, such as beta-blockers including timolol, betaxolol, levobetaxolol, carteolol, miotics including pilocarpine, carbonic anhydrase inhibitors, prostaglandins, seretonergics, muscarinics, dopaminergic agonists, adrenergic agonists including apraclonidine and brimonidine; anti-infective agents including quinolones such as ciprofloxacin, and aminoglycosides such as tobramycin and gentamicin; non-steroidal and steroidal anti-inflammatory agents, such as suprofen, diclofenac, ketorolac, rimexolone and tetrahydrocortisol; growth factors, such as EGF; immunosuppressant agents; and anti-allergic agents including olopatadine.

The ophthalmic drug may be present in the form of a pharmaceutically acceptable salt, such as timolol maleate, brimonidine tartrate or sodium diclofenac. Compositions of the present invention may also include combinations of ophthalmic drugs, such as combinations of (i) a beta-blocker selected from the group consisting of betaxolol and timolol, and (ii) a prostaglandin selected from the group consisting of latanoprost; 15-keto latanoprost; fluprostenol isopropyl ester (especially 1R-[1α(Z),2β(1E,3R*),3α,5α]-7-[3,5-dihydroxy-2-[3-hydroxy-4-[3-(trifluoromethyl)-phenoxy]-1-butenyl]cyclopentyl]-5-heptenoic acid, 1-methylethyl ester); and isopropyl [2R(1E,3R),3S(4Z),4R]-7-[tetrahydro-2-[4-(3-chlorophenoxy)-3-hydroxy-1-butenyl]-4-hydroxy-3-furanyl]-4-heptenoate.

Although the amount of drug included in the compositions of the present invention will be whatever amount is therapeutically effective and will depend upon a number of factors, including the identity and potency of the chosen drug, the total concentration of drug will generally be about 5% (w/w) or less. Alternatively, the compositions of the present invention may be formulated without ophthalmic drugs, in which case the compositions may serve in the prevention or treatment of dry eye.

In addition to xanthan gum and any ophthalmic drug, the compositions of the present invention may include other components. For example, the compositions may include one or more pharmaceutically acceptable buffering agents, preservatives (including preservative adjuncts), tonicity-adjusting agents, surfactants, solubilizing agents, stabilizing agents, comfort-enhancing agents, emollients, pH-adjusting agents and/or lubricants. The compositions of the present invention may also contain drug carrier substrates, such as cation exchange resins, anion exchange resins, encapsulating microspheres, insoluble drug particles, gel particles and polymeric drug complexes.

As mentioned above, the identity and amount of additional ingredients in the xanthan gum compositions of the present invention can effect the compositions' 15 ability to gel upon contact with the eye. In this regard, the compositions of the present invention should be formulated so that their total ionic strength is approximately 120 mM or less, and preferably about 94 mM or less. Compositions containing xanthan gum that have a total ionic strength greater than about 120 mM are unlikely to gel upon contact with the eye. Total ionic strength is calculated according to the well accepted formula: Ionic strength=$0.5\Sigma m_i Z_i^2$, where $m_i$ is the molar concentration of ionized specie i with a valency of $Z_i$. As used herein, "total ionic strength" excludes any contribution from xanthan gum itself.

Xanthan gum is generally available in at least two grades from some commercial suppliers, a food or industrial grade and a pharmaceutical grade. It is preferable to polish filter even pharmaceutical grade materials so that the finished pharmaceutical product will have increased clarity. As one skilled in the art appreciates, the appropriate filter size for polish filtration depends upon the size of the undesired impurities contained in raw material. For example, in the case of a solution composition, it has been found that the Rhodigel Clear grade of xanthan gum from Rhone-Poulenc Inc. should be filtered through a 0.45 μm filter in order to remove cell debris and impurities. Multiple stages of filters can be used to increase the overall efficiency of the polish filtration process.

If xanthan gum is to be sterilized using steam or heat, the length of time xanthan is exposed to elevated temperatures is preferably minimized. By using relatively higher target temperatures and shorter residence times to achieve a desired sterilization, including relatively rapid ramp up and ramp down times, the effect of elevated temperatures upon xanthan gum's ability to gel can be reduced.

The following examples are presented to illustrate further various aspects of the present invention, but are not intended to limit the scope of the invention in any respect.

EXAMPLES

Example 1
Measurement of Gel Strength of Xanthan Gum Raw Material Using Lysozyme ("the Lysozyme Gel Strength Test").

An in vitro test is used to measure the gel strength (elastic modulus, G') of xanthan gum raw material after mixing with lysozyme, a protein found in tears. While not wishing to be bound by any theory, it is believed that xanthan gum undergoes an ionic interaction with lysozyme to form a gel. The gel strength is measured as follows:

Prepare a 0.6% (w/w) aqueous solution of xanthan gum containing 0.5% (w/w) NaCl using purified water. Add 2.0 g of the aqueous solution of xanthan gum to 4.0 g of a freshly prepared 0.2% (w/w) solution of chicken lysozyme (chicken lysozyme in purified water) contained in a 20 mL scintillation vial. Immediately mix the resulting sample for 30 seconds on a wrist action shaker using the shaker parameters listed below (shaking is a critical step). Following shaking, allow the sample to stand for 3–4 minutes. Perform remaining steps as quickly as possible. Gently isolate the resulting gelatinous mass by pouring the contents of the scintillation vial onto a 180 mm nylon mesh filter and allow to drain for approximately 10 seconds. Gently slide the filtered sample onto the center of the stage of a Bohlin constant stress rheometer. Gently lower the upper plate of the rheometer to spread the sample over the entire bottom surface of the upper plate. Allow the sample to equilibrate for 4 minutes. Measure elasticity in the oscillation mode using the instrumental parameters shown below. Average the results for 3–8 replicate samples to obtain a final result.

| Parameters for Wrist Action Shaker (Lab-Line 3589-1 or equivalent) | |
| --- | --- |
| Cycle (up & down) time | 700–750 rpm |
| Vertical Displacement | 10–12 mm |
| Arm Length | 14–15 cm |
| Geometry | Clamp at 45° angle from vertical in a plane perpendicular to arm motion |
| Parameters for Bohlin Constant Stress Rheometer (Bohlin CS-10 or equivalent) | |
| Plate | 40 mm parallel geometry, stainless steel |
| Gap | 1.3 mm |
| Mode | Oscillation |
| Frequency | 1 Hz |
| Shear Stress | 0.25 Pa |
| Temperature | 34° C. |
| Delay Time | 5 seconds |
| Wait Time | 10 seconds |
| Resolution | High |

Figure 2:
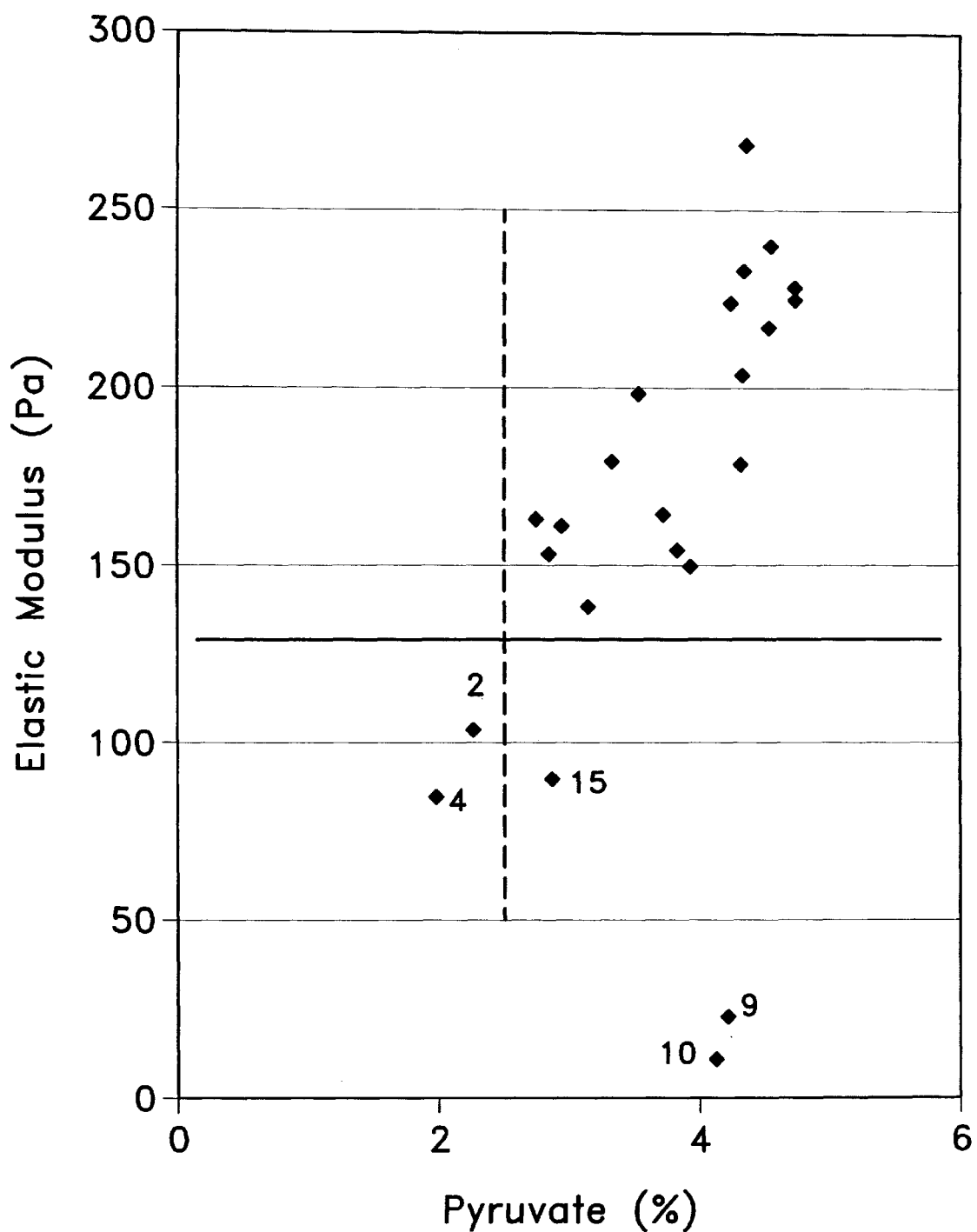
FIG. 2 shows the relationship between elastic modulus (G', Pa) and pyruvate content for xanthan gum.

The gel strength of 23 different lots of xanthan gum obtained from various suppliers was tested using the Lysozyme Gel Strength Test, and gel strength (elastic modulus, G') results for each lot are listed in Table 1. These results are also shown in FIG. 1 (elastic modulus vs. acetate content) and FIG. 2 (elastic modulus vs. pyruvate content). Initial bound acetate and pyruvate content was measured using ion exclusion HPLC with ultraviolet detection (205 nm). Xanthan gum raw material was dissolved in purified water and analyzed for hydrolyzed ("free") acetate and pyruvate content. A separate solution of the same lot of xanthan gum was subjected to an acid hydrolysis step prior to HPLC analysis to determine total acetate and pyruvate content. Bound acetate and pyruvate are calculated by the differences between the total and free values.

TABLE 1

| LOT # | INITIAL BOUND PYRUVATE (%) | INITIAL BOUND ACETATE (%) | ELASTIC MODULUS G' (Pa) |
| --- | --- | --- | --- |
| 1 | 3.4 | 5.1 | 180 |
| 2 | 2.3 | 5.5 | 104 |
| 3 | 2.8 | 5.2 | 164 |
| 4 | 2 | 4.7 | 85 |
| 5 | 3 | 5 | 162 |
| 6 | 3.6 | 5.7 | 199 |
| 7 | 3.2 | 6.3 | 139 |
| 8 | 2.9 | 4.8 | 154 |
| 9 | 4.2 | 3.7 | 22 |
| 10 | 4.1 | 3.5 | 10 |
| 11 | 4 | 5.4 | 150 |
| 12 | 4.4 | 5.2 | 179 |
| 13 | 3.8 | 4.6 | 165 |
| 14 | 3.9 | 4.9 | 155 |
| 15* | 2.9 | 5.6 | 90 |
| 16 | 4.3 | 5.6 | 224 |
| 17 | 4.6 | 5.4 | 217 |
| 18 | 4.4 | 5.9 | 204 |
| 19 | 4.4 | 5 | 233 |
| 20 | 4.6 | 5.4 | 240 |
| 21 | 4.8 | 5.5 | 228 |
| 22 | 4.8 | 5.4 | 225 |
| 23 | 4.4 | 5.2 | 268 |

*This sample was expired; it was >11 years old.

Example 2
Ophthalmic Compositions

The ophthalmic compositions shown below in Table 2 can be prepared according to the present invention. All values are expressed as % w/v unless otherwise noted.

TABLE 2

| INGREDIENT | A | B | C (vehicle) |
| --- | --- | --- | --- |
| Timolol Maleate | 0.34 | 0.68 | — |
| Benzododecinium Bromide | 0.012 | 0.012 | 0.012 |
| Xanthan Gum | 0.6 | 0.6 | 0.6 |
| Tromethamine | 0.72 | 0.8 | 0.6 |
| Boric Acid | 0.3 | 0.3 | 0.3 |
| Mannitol | 4.35 | 3.75 | 4.4 |
| Polysorbate 80 | 0.05 | 0.05 | 0.05 |
| Purified Water | q.s. 100 | q.s. 100 | q.s. 100 |

| INGREDIENT | D | E | F |
| --- | --- | --- | --- |
| Xanthan Gum | 0.3 | 0.3 | 0.3 |
| HPMC* | — | — | 0.25 |
| Tromethamine | q.s. pH 6–8 | q.s. pH 6–8 | q.s. pH 6–8 |
| Mannitol | q.s. 250–300 mOsm | q.s. 250–350 mOsm | q.s. 250–350 mOsm |
| Glycerin | — | 0.2 | — |
| Purified Water | q.s. 100 | q.s. 100 | q.s. 100 |

| INGREDIENT | G | H | I |
| --- | --- | --- | --- |
| Xanthan Gum | 0.6g | 0.6 g | 0.6g |
| Cartelol | — | 1.05 g | 2.1g |
| Mannitol | — | 3.4 g | 3 g |
| Sorbitol | 4.5g | — | — |
| Boric Acid | 0.3g | 0.3 g | 0.3 g |
| Tromethamine | 0.7g | 0.561 | 0.54 g |

TABLE 2-continued

| | | | |
|---|---|---|---|
| Polysorbate 80 | 0.05 g | 0.05 g | 0.05 g |
| Benzododecinium Bromide | 0.012g | 0.012g | 0.012 g |
| Purified Water | qs to 100 g | qs to 100 g | qs to 100 g |
| pH | 7.5 | 6.7 | 6.7 |

| INGREDIENT | J (% w/w) |
|---|---|
| Polysorbate 80 | 0.05 |
| Xanthan Gum | 0.4–0.8 |
| Mannitol | 4.4 |
| Boric Acid | 0.3 |
| Tromethamine | 0.6 |
| Benzalkonium Chloride | 0.01 + 10% xs |
| Purified Water | |

| INGREDIENT | K |
|---|---|
| Olopatadine HCl | 0.111 |
| Xanthan Gum | 0.6 |
| Boric Acid | 0.3 |
| Mannitol | 4.4 |
| Tromethamine | 0.64 |
| Polysorbate 80 | 0.05 |
| Benzalkonium Chloride | 0.01 |
| Tromethamine | q.s. pH 7 |
| Hydrochloric Acid | q.s. pH 7 |
| Purified Water | q.s. to 100 |

*HPMC = hydroxypropyl methylcellulose

Example 3
Effect of Acetate Content on Gel Strength

Figure 3:
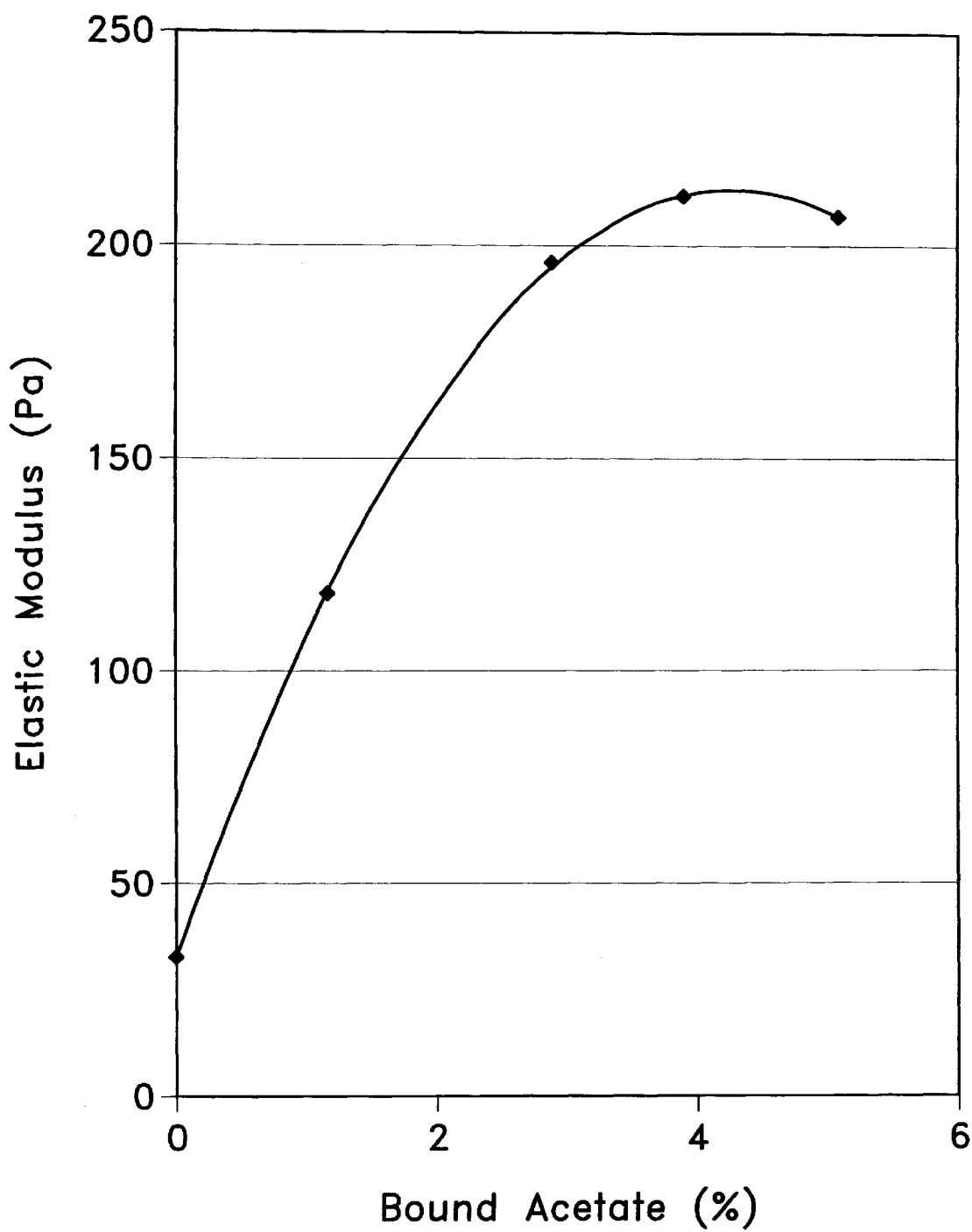
FIG. 3 shows the relationship between elastic modulus (G', Pa) and bound acetate content for xanthan gum.

To demonstrate the effect of bound acetate content on the ability of xanthan gum to gel upon contact with lysozyme, xanthan gum having an initial bound acetate content of 5.2% was progressively deacylated as follows. A stock solution containing 0.75 wt % xanthan gum and 0.4625 wt % NaCl was prepared. To the 40.0 g of stock solution, the indicated amount of 1N NaOH was added. The solution was stirred for ten minutes at room temperature. Then the indicated amount of 1N HCl was added. The pH of the solution was adjusted to 7 with 0.1N NaOH. Then the indicated amount of sodium chloride was added, followed by purified water to adjust sample size to 50.0 g and stirring for one hour. Each of the five solutions had final concentrations of 0.6% xanthan gum and 0.5% NaCl. The results are shown below in Table 3 and in FIG. 3.

The NaCl concentration contributions from the stock solution and from NaOH/HCl are also shown below. The approximate weight of the NaCl contributed to the composition by NaOH/HCl was calculated as $(MW_{NaCl} \times$ weight of 1N NaOH added)/1000.

TABLE 3

| | SAMPLE | | | | |
|---|---|---|---|---|---|
| | A | B | C | D | E |
| 0.75% xanthan gum, 0.46% NaCl stock, g | 40 | 40 | 40 | 40 | 40 |
| 1N NaOH, g | 0 | 0.11 | 0.2 | 0.5 | 1.1 |
| 1N HCl, g | 0 | 0.11 | 0.2 | 0.5 | 1.1 |
| NaCl, g | 0.064 | 0.0576 | 0.0524 | 0.0349 | 0 |
| Purified Water, g | q.s. 50 | q.s. 50 | q.s. 50 | q.s. 50 | q.s.50 |
| % NaCl from Stock | 0.37 | 0.37 | 0.37 | 0.37 | 0.37 |
| % NaCl from NaOH & HCl* | 0 | 0.01287 | 0.0234 | 0.0585 | 0.1287 |
| % NaCl added to sample after HCl | 0.128 | 0.1152 | 0.1048 | 0.0698 | 0 |
| % Total NaCl | 0.498 | 0.49807 | 0.4982 | 0.4983 | 0.4987 |
| Osmolality, mOsm | 181 | 182 | 182 | 183 | 188 |
| Free Pyruvate | None@ | None@ | None@ | None@ | None@ |
| Free Acetate, % of xanthan wt. | 0 | 1.2 | 2.2 | 3.9 | 5.2 |
| Gel Strength (G', Pa) (individual) | 207 | 223 | 181 | 97 | 38 |
| | 195 | 232 | 81* | 59* | 41 |
| | 189 | 224 | 194 | 128 | 28 |
| | 235 | 168 | 214 | 134 | 28 |
| Gel Strength (G', Pa) (Average) | 207 | 212 | 196 | 120 | 34 |

*Not considered for calculation of average because it is 3 standard deviations away from the average of the remaining three readings.
@Below detection limit.

Example 4

Effect of Other Composition Ingredients and Xanthan Gum Concentration on Gel Strength To demonstrate the effect of composition ingredients and xanthan gum concentration on gel strength, the formulations shown below were prepared and tested using the Lysozyme Gel Strength Test. The results are shown in Table 4 (all amounts are expressed in % w/w).

TABLE 4

| | SAMPLE | | | | | | | | |
|---|---|---|---|---|---|---|---|---|---|
| INGREDIENT | A | B | C | D | E | F | G | H | I |
| Betaxolol HCl | — | 0.28 | — | — | — | — | — | — | — |
| (S)-Betaxolol HCl | 0.168 | — | 0.28 | 0.4 | 0.56 | 0.84 | 0.75 | 0.84 | 0.84 |
| Xanthan Gum | 0.6 | 0.6 | 0.6 | 0.6 | 0.6 | 0.6 | 0.6 | 0.6 | 1 |
| Amberlite IRP-69 | — | 0.25 | 0.25 | 0.45 | 0.65 | 1.5 | 2.5 | 1.125 | 1.5 |
| Mannitol | 4 | 4 | — | — | — | — | 3.9 | 3.7 | 3.7 |
| Glycerine | — | — | 1.85 | 1.8 | 1.75 | 1.65 | — | — | — |
| Boric Acid | 0.3 | — | 0.4 | 0.4 | 0.4 | 0.4 | 0.1 | 0.3 | 0.3 |
| Edetate Disodium | 0.01 | 0.01 | — | — | — | — | — | 0.01 | 0.01 |
| Edetic Acid | — | — | 0.05 | 0.05 | 0.05 | 0.05 | — | — | — |
| Polysorbate 80 | 0.05 | — | 0.05 | 0.05 | 0.05 | 0.05 | — | 0.05 | 0.05 |
| N-Lauroylsarcosine | — | — | 0.03 | 0.03 | 0.03 | 0.03 | — | 0.03 | 0.03 |
| Benzalkonium Chloride | — | 0.011 | 0.011 | 0.011 | 0.011 | 0.011 | — | 0.01 | 0.01 |
| Benzododecinium Bromide | 0.012 | — | — | — | — | — | — | — | — |
| Tromethamine | 0.56 | 0.14 | 0.39 | 0.62 | 0.56 | 0.94 | 1.76 | 1.14 | 1.44 |
| Purified Water | q.s. | q.s. | q.s. | q.s. | q.s. | q.s. | q.s. | q.s. | q.s. |

TABLE 4-continued

| | SAMPLE | | | | | | | | |
|---|---|---|---|---|---|---|---|---|---|
| INGREDIENT | A | B | C | D | E | F | G | H | I |
| | 100 | 100 | 100 | 100 | 100 | 100 | 100 | 100 | 100 |
| Gel Strength (G', Pa) | 140 | 128 | 34 | 4 | 2 | 1 | 1 | 2 | 72 |

Example 5
Gel Strength Correlation between Xanthan Gum Raw Material and Finished Product To demonstrate the correlation between the gel strength formed by xanthan gum raw material using the Lysozyme Gel Strength Test and that formed by finished product, the gel strength of Compositions A and B of Example 2 (following steam sterilization) were evaluated. The results are shown below in Table 5.

TABLE 5

| Sample | Raw Material G' (Pa) | Composition A G' (Pa) | Composition B G' (Pa) |
|---|---|---|---|
| 1 | 180 | 114 (n = 23, RSD = 12%) | 100 (n = 26; RSD = 10%) |
| 2 | 104 | 92 (n = 9; RSD = 12%) | 67 (n = 9; RSD = 13%) |
| 3 | 164 | 115 (n = 1) | 73 (n = 1) |
| 4 | 85 | 46 (n = 2) | 32 (n = 1) |
| 5 | 199 | 100 (n = 2) | 104 (n = 2) |

Example 6
Calculation of Total Ionic Strength

The ionic strength contributions from the different ions of Compositions A–C of Table 2 were calculated using a pH=6.9 and are shown in Table 6. At this pH, the following charged species (excluding xanthan gum itself) are present in the composition:

1. mannnitol-boric acid-tromethamine buffer: monovalent anionic mannitol borate complex adjusted to pH 6.9 with monovalent cation tromethamine. This contributes an ionic strength of about 46 mM to all three compositions.

2. benzododecinium bromide: because the concentration of this ingredient is so small and because the valence is 1 for both the benzododecinium and bromide ions, the ionic strength contribution to each of the three compositions from this is insignificant.

3. timolol maleate: at pH 6.9, timolol maleate would be present as monovalent timolol cations, divalent maleate anions and monovalent maleate anions. The ionic strength contribution of timolol maleate and the amount of tromethamine needed to adjust the pH of timolol maleate to pH 6.9 is approximately 22 mM for position A and 42 mM for Composition B.

TABLE 6

| IONS | pKa | % Monovalent at pH 6.9 | % Divalent at pH 6.9 | A | B | C |
|---|---|---|---|---|---|---|
| Timolol | 9.21 | 99.5 | | 3.9 | 7.9 | 0.0 |
| Maleate* | 6.33 | 21.2 | 78.8 | 13.0 | 26.1 | 0.0 |
| Tromethamine | 8.08 | 93.8 | | 27.8 | 30.9 | 23.2 |
| Boric Acid** | 5.7–5.85 | 94.1 | | 22.8 | 22.8 | 22.8 |
| Total | | | | 67.6 | 87.7 | 46.0 |

*Second pKa
**pKa of boric acid in presence of 3.75 to 4.4 wt. % mannitol.

Example 7
Effect of Ionic Strength on Xanthan Gum's Ability to Gel

Figure 4:
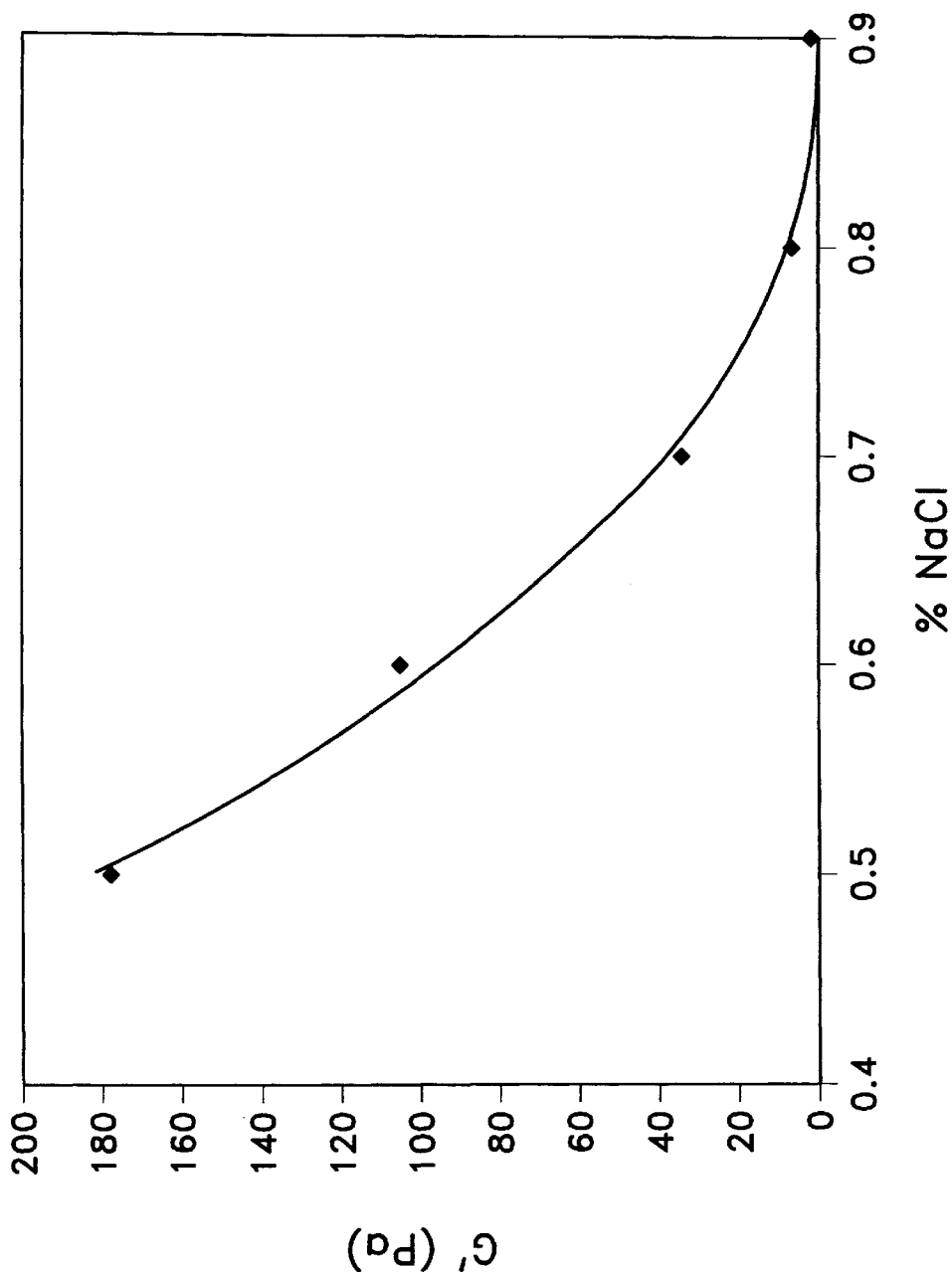
FIG. 4 shows the relationship between elastic modulus (G', Pa) and NaCl concentration.

The effect of total ionic strength on xanthan gum's ability to gel was evaluated by varying the concentration of NaCl in the 0.6% (w/w) solution of xanthan gum in the Lysozyme Gel Strength Test. Specifically, the Lysozyme Gel Strength Test described in Example 1 was performed five times for the same lot of xanthan gum, but each time the NaCl concentration was different. As a control sample, a 0.6% (w/w) xanthan gum solution (same lot of xanthan gum as in the previous five samples) was tested using the Lysozyme Gel Strength Test (0.5% (w/w) of NaCl), except that it was not mixed with any chicken lysozyme. The results are shown below in Table 7 and in FIG. 4. A 0.7% (w/w) solution of NaCl has an ionic strength of approximately 120 mM [0.5 ((7/58.5×1000)+(7/58.5×1000))=119.6].

TABLE 7

| NaCl concentration (w/w) | Elastic Modulus (G', Pa) |
|---|---|
| 0.5 | 178 |
| 0.6 | 106 |
| 0.7 | 35 |
| 0.8 | 6.3 |
| 0.9 | 2.6 |
| Control | 13 |

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

We claim:

1. An improved ophthalmic composition comprising xanthan gum, wherein the improvement comprises the composition having a total ionic strength of about 120 mM or less and the xanthan gum having an initial bound acetate content of at least about 4% and an initial bound pyruvate content of at least about 2.5%, provided that the composition does not contain locust bean gum.

2. The composition of claim 1 wherein the amount of xanthan gum is from about 0.1 to about 1% (w/w).

3. The composition of claim 1 further comprising an ophthalmic drug.

4. The composition of claim 3 wherein the drug is selected from the group consisting of anti-glaucoma agents; anti-infective agents; non-steroidal and steroidal anti-inflammatory agents; growth factors; immunosuppressant agents; and anti-allergic agents.

5. The composition of claim 4 wherein the drug is selected from the group consisting of timolol; brimonidine; tobramycin; ciprofloxacin; rimexolone; olopatadine; latanoprost; 15-keto-latanoprost; fluprostenol isopropyl ester; isopropyl [2R(1E,3R),3S(4Z),4R]-7-[tetrahydro-2-[4-(3-chlorophenoxy)-3-hydroxy-1-butenyl]-4-hydroxy-3-furanyl]-4-heptenoate; and the pharmaceutically acceptable salts thereof.

6. The composition of claim 1 further comprising one or more agents selected from the group consisting of buffering agents; preservatives; tonicity-adjusting agents; surfactants; solubilizing agents; stabilizing agents; comfort-enhancing agents; emollients; pH-adjusting agents; lubricants; and drug carrier substrates.

7. The composition of claim 1 wherein the xanthan gum forms a gel having an elastic modulus (G') of approximately 130 Pa when measured in the Lysozyme Gel Strength Test.

8. The composition of claim 1 wherein the composition has a total ionic strength of about 94 mM or less.

9. The composition of claim 1 wherein the composition comprises tobramycin or a pharmaceutically acceptable salt of tobramycin, a preservative, a pH-adjusting agent, a tonicity adjusting agent, and xanthan gum.

10. The composition of claim 1 wherein the composition comprises timolol or a pharmaceutically acceptable salt of timolol, a preservative, a pH-adjusting agent.

11. The composition of claim 10 wherein the composition comprises timolol maleate, benzododecinium bromide, tromethamine, boric acid, mannitol, and polysorbate 80.

12. The composition of claim 1 wherein the composition is intended for treating dry eye and comprises a pH-adjusting agent and a tonicity adjusting agent.

13. The composition of claim 12 wherein the amount of xanthan gum is 0.4–0.8% (w/w).

* * * * *